United States Patent [19]

Godfroid et al.

[11] 3,969,529
[45] July 13, 1976

[54] PHENOXYACETIC ACID DERIVATIVES AS DIURETIC AGENTS

[75] Inventors: Jean Jacques Godfroid, Noisy-le-Sec; Jean Eugène Thuillier, Paris, both of France

[73] Assignee: C.E.R.P.H.A., Arcueil, France

[22] Filed: Apr. 28, 1975

[21] Appl. No.: 572,311

Related U.S. Application Data

[60] Continuation of Ser. No. 353,986, April 24, 1973, abandoned, which is a division of Ser. No. 78,976, Oct. 7, 1970, Pat. No. 3,758,506.

[30] Foreign Application Priority Data

Oct. 10, 1969  France .............................. 69.34760

[52] U.S. Cl. ................................ 424/275; 424/285

[51] Int. Cl.² ......................................... A61K 31/38
[58] Field of Search ............................ 424/275, 285

[56] References Cited
UNITED STATES PATENTS

3,751,430  8/1973  Libis et al. ........................... 424/275

Primary Examiner—Frederick E. Waddell
Attorney, Agent, or Firm—Stevens, Davis, Miller & Mosher

[57] ABSTRACT

4-[(2-furyl-keto), (2-thienyl-keto) or (2-(5-methyl-thienyl)-keto], 2,3 dichloro phenoxyacetic acids, their alkali metal salts and pharmaceutically acceptable base addition salts, are valuable as strong diuretics.

8 Claims, No Drawings

PHENOXYACETIC ACID DERIVATIVES AS DIURETIC AGENTS

This is a continuation of application Ser. No. 353,986, filed Apr. 24, 1973, now abandoned, which application is a divisional application of Ser. No. 78,976 filed Oct. 7, 1970 now U.S. Pat. No. 3,758,506.

This invention relates to new phenoxyacetic acid derivatives.

According to the present invention there is provided a phenoxyacetic acid of the general formula

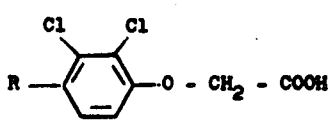

wherein R signifies 2-furyl keto, 2-thienyl keto, or 2(5-methyl thienyl) keto, an alkali metal salt of a said acid, or an addition salt of a said acid with a pharmaceutically acceptable base.

Of particular value as pharmaceutically acceptable bases are piperazine, N-methyl piperazine and N-methyl glucamine.

To prepare the new compounds, one of the esters may be saponified which is obtained by condensing with an ester of a haloacetic acid, particularly with ethyl chloracetate, the 2-furyl, 2-thienyl or 2-(5-methyl thienyl) 2,3-dichloro hydroxyphenyl ketone resulting from the condensation of 2,3-dichloro-anisole with the chloride of furan 2-carboxylic acid, thiophene-2-carboxylic acid or 5-methyl-thiophene-2-carboxylic acid, in the presence of aluminium chloride, and then demethylating the ketophenolic ether so formed by the action of aluminium chloride. The phenoxyacetic acid is then freed from its salt by reaction with strong acid.

The reaction between the dichloro-anisole and the acid chloride can be carried out in solvents such as carbon disulphide or methylene chloride, or even without a solvent. The methoxy phenyl ketone obtained can be demethylated, for example by the action of aluminium chloride in a solvent such as benzene or methylene chloride.

Instead of reacting an ester of a halogenoacetic acid with a ketophenol, the sodium salt of this phenol may be prepared by the action of sodium or potassium hydroxide, and condensing the salt with, for example, sodium or potassium monochloracetate in an aqueous or alcoholic medium.

The following examples will serve to illustrate the invention. Temperatures are given in degrees centigrade. Melting points were determined by the Kofler block method unless otherwise stated.

EXAMPLE 1

4-(2-furyl keto) 2,3-dichloro phenoxyacetic acid (CE 3598)

a. To a solution of 44.2 g of 2,3-dichloro-anisole (0.25 mole), 65 g of furan 2-carboxylic acid chloride (0.5 mole) and 250 ml carbon disulphide, there was added, in small portions, 66.6 g (0.5 mole) of anhydrous aluminium chloride. The temperature during the addition was kept at 25°. The mixture was then stirred at ambient temperature for 5 hours. The mixture was left overnight and then heated for 1 hour at 55° (reflux of carbon disulphide). The mixture was cooled, and the solution then hydrolised with 500 ml of crushed ice containing 50 ml of concentrated hydrochloric acid. The precipitate formed is dried and washed with a 30% solution of caustic soda, and then with distilled water. 64.7 g of grey crystals were obtained, M.Pt.148°. Recrystallisation in methyl ethyl ketone gave 57.8 gm of crystals (yield 85%) melting at 150°.

b. to a solution of 40.6 g (i.e. 0.15 mole) of the product just obtained in 350 ml dethiophenated benzene, there was added, in small portions, 60 gm of anhydrous aluminium chloride. The mixture was then placed under reflux for two hours. The solution was hydrolized with 40 gm of ice. The precipitate formed is extracted and taken up in a 10% solution of sodium hydroxide, then reprecipitated in a 10% hydrochloric acid solution. There was thus obtained 34.8 gm of crystals which were recrystallised in 200 ml benzene. 29.1 gm of crystals were obtained (yield 75%) melting at 129° – 130°.

c. a solution of sodium ethylate is prepared by dissolving 1.50 gm of sodium in 100 ml absolute ethanol. There was then added 16.7 gm phenol (0,065 mole) and then 9.6 gm of ethyl chloracetate. The solution was refluxed for 14 hours. Extraction was carried out hot (elimination of sodium chloride) the crystals precipitating during cooling of the filtrate. There were collected 15 gm of crystals (yield of crude product 67%). After recrystallisation in isopropanol, 12.9 gm (58%) was obtained, melting at 90°.

d. 10 gm of the preceding ester were dissolved in the hot in 300 ml of ethanol at 95°. 4 ml of 30% caustic soda were added. A copious white precipitate formed. The mixture was refluxed for 30 minutes. The crystals were extracted and washed with hot alcohol. They were dissolved in 100 ml hot water and the acid precipitated with hydrochloric acid. Recrystallisation in 15 ml 50% ethanol gave 8.6 gm of crystals (yield 95%) melting at 176°. The sodium salt could be purified directly by recrystallisation in water (7 gm per 75 ml water). Melting point 260° – 265° (Maquenne block, without correction).

EXAMPLE 2

4-(2-thienyl keto) 2,3-dichloro phenoxyacetic acid (CE 3624)

a. to a solution of 55 gm of 2,3-dichloroanisole (0.31 mole), 91 gm of thiophene 2-carboxylic acid chloride (0.62 mole) and 180 ml carbon disulphide, there was added little by little 82.7 gm of anhydrous aluminium chloride, keeping the temperature at about 25°. The reaction mixture was stirred at ambient temperature for five hours, left standing overnight and then heated for one hour at 55°. The solution was cooled and hydrolised by 250 gm of ice and 60 ml concentrated hydrochloric acid. The precipitate formed is treated with a 30% solution of caustic soda, then washed with water. After recrystallisation in 95% ethanol, 88.6 gm (yield 92%) of crystals are obtained melting at 108°.

The process can also be carried out without solvent keeping the same proportions of reactants, or in methylene chloride by adding a slight excess of aluminium chloride powder to a solution of one mole of dichloro-anisole and one mole of acid chloride.

b. 88.6 gm of the ketone just obtained (0.308 mole) were dissolved in 300 ml of benzene, 123.5 gm of aluminium chloride was added in small doses, and the mixture was boiled under reflux for two hours.

The reaction mixture was hydrolysed by 500 gm ice; the precipitive is extracted and taken up in a 10% aqueous caustic soda solution. The benzene phase obtained after hydrolysis is concentrated. The oil obtained is treated as above and the precipitate added to the other. The crystals were recrystallised in 50% ethanol 60 gm of product were obtained, melting at 142°.

The reaction may also be effected with excellent yields in methylene chloride.

c. a solution of sodium ethylate was prepared by dissolving 3.45 gm of sodium (0.15 mole) in 200 ml absolute ethanol. There was then added 31 gm of the preceding phenol (0.15 mole) then 25.8 gm ethyl chloroacetate. The mixture was refluxed for 15 hours. Hot extraction was carried out to eliminate the sodium chloride.

The ester precipitated on cooling the filtrate. The product was recrystallised once in isopropanol to give 29.4 gm of crystals melting at 58°. The pure product melts at 63° – 64°.

The ester was dissolved in a solution of 300 ml 95% ethanol and 9 ml of 10N caustic soda. The mixture was boiled under reflux for 30 minutes. The precipitate of the sodium salt of the acid which forms in the cold was extracted and taken up in warm water. The free acid was then precipitated in mineral acid medium. After recrystallisation in 50% ethanol, it melted at 148° – 9°.

An alternative method is to start from an aqueous solution of phenate prepared by the action of caustic soda, add to it while boiling a slight excess of sodium monochloracetate, and, having maintained an alkaline pH for 3 hours refluxing, isolating the precipitate formed by hot filtration. The acid is freed from its salt by addition of a strong mineral acid to a hot aqueous solution, and extracted hot with dichloroethane. After recrystallisation in purified dichloroethane, the acid melts at 157°.

The sodium salt of the acid melts at 270° and the potassium salt at 290°. These melting points, determined by Maquenne block, have not been corrected.

The piperazine addition salt (prepared in ethanol with two molecules of acid per one of piperazine) melts at 216°. The N-methyl piperazine addition salt (prepared starting from the acid and the base in equimolecular proportions), melts at 140°, while the N-methyl glucamine addition salt, also prepared with an equimolecular proportion of acid and base, does not crystallise.

EXAMPLE 3

Operating as in Example 1, and starting from 2,3-dichloro-anisole and 5-methyl-thiophene-2-carboxylic acid chloride, there was obtained the compound CE 3649, which melted at 176° after recrystallisation from 50% ethanol.

The hydroxyphenyl ketone intermediate in this synthesis, melts at 168°, and the phenoxyacetic ester at 100°.

ACUTE TOXICITY

The three compounds were administered in the usual way to lots of 10 male mice of average weight 20 gm. Mortality was assessed after 24 hours for the intravenous toxicity and after 48 hours for toxicity per os. The results are given in Table I.

TABLE 1

| Code | Acute toxicity in mice LD50 intravenous mg/kg —mice | LD50 per os g/kg mice |
|---|---|---|
| CE3598 | 450 | 1.5 |
| CE3624 | 225 | 1.275 |
| CE3649 | 580 | 2.9 |

II - TOLERANCE

Administered in doses from 50 to 200 mg/kg via the digestive tract to lots of three dogs for 5 days, the products CE 3598, CE 3624 and CE 3649 gave rise to no symptoms which would indicate any injurious activity.

III - PHARMACOLOGY

A - GENERAL PHARMACOLOGY

No pharmacological activity other than that described herein has been observed.

Administered either orally or intravenously, the three compounds had practically no action in screening tests designed to reveal any activity such as analgesic, antiinflammatory, hypoglycemiant, hypochloesterolemiant, antispasmodic, antichlolinergic, cardiovascular, psychotropic, etc.

However, in anaesthetised dogs, the injection of one or other of the three compounds at doses of from 10 – 50 mg/kg, produced a fall in tension, in part in agreement with the diuretic activity and in part with an action peculiar to this type of molecule.

B - DIURETIC ACTIVITY a. In mice

The three compounds CE 3598, CE 3624, CE 3649 can be shown to be diuretic at doses of from 1 – 50 mg/kg for the first. For example, for CE 3624, diuresis is doubled at 25 mg/kg and quintupled at 50 mg/kg, while for CE 3649, its activity is a quarter of that of CE 3624.

b. In dogs

In dogs anaesthetized with mebubarbital (30 mg/kg), the diuretic action provoked by CE 3624 is extremely substantial and precocious. The doses injected were of the order of 5 – 30 mg/kg. In most cases, diuresis was decupled for more than 2 hours.

As far as CE 3598 is concerned, in the case of an intravenous injection, a substantial diuretic action is provoked in the first 15 minutes, at weak doses of the order of 10 mg/kg. This increase in diuresis is still perceptible 2 hours after injection, the peak of activity being between 15 and 30 minutes. The size of the increase may reach 6 to 7 times, even 10 times, the base diuresis.

In the case of intraduodenal injection or administration per os, the active doses are relatively the same as by intravenous administration.

2. In non-anaesthetized dogs

After hydration with 500 ml physiological water and calculation of the diuresis for 2 hours, CE 3624, CE 3649 and CE 3598 were administered per os at doses of from 10 to 100 mg/kg. In these conditions, diuresis was strongly increased.

For CE 3624 at 20 mg/kg, the diuresis was quintupled for 3 hours; the same result was obtained at 10 mg/kg. For CE 3649, at the same doses, the diuresis was only doubled. The doses of CE 3598 administered per os were 25, 50 and 100 mg/kg. The increase in diuresis was effective during the first hour, and still notable 3 hours after administration of the product.

The 4-(2-furyl keto) 2,3-dichloro phenoxyacetic acid and its salts, 4-(2-thienyl keto) 2,3-dichloro phenoxyacetic acid and 4-[2(5-methyl thienyl) keto] 2,3-dichloro phenoxyacetic acid and their salts are useable in human and veterinary therapy as diuretics, in particular in all cases requiring the use of powerful diuretics. Their mode of operation, by inhibiting the reabsorption of sodium in the proximal tube and the ascending portion of Henles tube is of great interest in hydrosodic reactions and nephrotic oedemas.

These compounds can be used as active principles associated or not with other appropriate active principles, in the principal pharmaceutically suitable forms, such as tablets, capsules, suppositories and injectable solutions.

For per os administration, for suppositories, and for injectable solutions the dose can be from 0.050 to 1 gm of active product.

The compounds can be administered in daily doses varying from 100 to 1500 mg; at these doses, they do not provoke any undesirable secondary phenomena; in particular, potassium loss is relatively weak.

Examples of typical formulations are as follows:

| Formulation 1 For tablets | |
|---|---|
| Active principle | 0.500 gm |
| potato starch | 0.020 gm |
| polyvinyl pyrrolidone | 0.020 gm |
| maize starch | 0.045 gm |
| talc | 0.020 gm |
| magnesium stearate | 0.015 gm |
| Formulation 2 For injectable solutions | |
| N-methyl piperazine salt of CE 3624 | 0.500 gm |
| distilled water | 2 ml. |

We claim as our invention:

1. A therapeutic composition in dosage form, particularly for increasing diuresis, which contains as active principle at least one phenoxyacetic acid compound selected from the group consisting of a phenoxyacetic acid of the formula

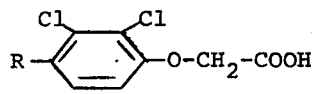

wherein R is 2-furyl keto, 2-thienyl keto or 2(5-methyl thienyl) keto, an alkali metal salt of said acid, and an addition salt of said acid with a pharmaceutically acceptable base together with a pharmaceutically acceptable diluent, said active principle being present in an amount of 0.050 to 1 g.

2. The therapeutic composition of claim 1 wherein said active principle is associated with an excipient for oral, endorectal or parenteral administration.

3. The therapeutic composition of claim 1 wherein the active principle is 4-(2-thienyl keto) 2,3-dichloro phenoxyacetic acid.

4. A process for treating a human or non-human in need of diuretic treatment which comprises the oral, endorectal or parenteral administration thereto, in a nontoxic amount sufficient to produce diuresis of a phenoxyacetic acid compound selected from the group consisting of a phenoxyacetic acid of the formula

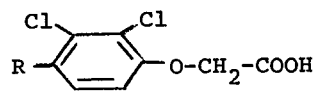

wherein R is 2-furyl keto, 2-thienyl keto or 2(5-methyl thienyl) keto, an alkali metal salt of said acid, and an addition salt of said acid with a pharmaceutically acceptable base.

5. The process of claim 4 wherein from 1–100 mg/kg of said phenoxyacetic acid compound is administered.

6. The process of claim 4 wherein said phenoxyacetic acid compound is administered in a daily dosage of from 100 to 1500 mg.

7. The process of claim 4 wherein said phenoxyacetic acid compound is 4-(2-thienyl keto) 2,3-dichloro phenoxyacetic acid.

8. A process for treating a human or non-human in need of diuretic treatment which comprises the oral, endorectal or parenteral administration thereto, in an amount of from 10–50 mg/kg, of a phenoxyacetic acid compound selected from the group consisting of a phenoxyacetic acid of the formula

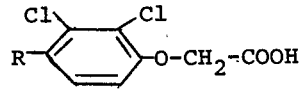

wherein R is 2-furyl keto, 2-thienyl keto or 2(5-methyl thienyl) keto, an alkali metal salt of said acid, and an addition salt of said acid with a pharmaceutically acceptable base.

* * * * *